United States Patent [19]
Yang

[11] Patent Number: 5,476,503
[45] Date of Patent: Dec. 19, 1995

[54] SENSE ARRAY INTELLIGENT PATCH LEAD FOR AN IMPLANTABLE DEFIBRILLATOR AND METHOD

[75] Inventor: Min-Yaug Yang, Monterey Park, Calif.

[73] Assignee: Pacesetter, Inc., Sylmar, Calif.

[21] Appl. No.: 218,956

[22] Filed: Mar. 28, 1994

[51] Int. Cl.$^6$ ........................................ A61N 1/05
[52] U.S. Cl. ........................................ 607/129
[58] Field of Search ........................ 607/129, 130, 607/131, 5

[56] References Cited

U.S. PATENT DOCUMENTS

| | | |
|---|---|---|
| 3,937,226 | 2/1976 | Funke . |
| 4,088,140 | 5/1978 | Rockland et al. . |
| 4,354,497 | 10/1982 | Kahn . |
| 4,577,634 | 3/1986 | Gessman . |
| 4,754,753 | 7/1988 | King . |
| 4,790,317 | 12/1988 | Davies . |
| 5,193,535 | 3/1993 | Bardy et al. . |
| 5,247,945 | 9/1993 | Heinze et al. ............... 607/129 |
| 5,257,621 | 11/1993 | Bardy et al. ............... 607/5 |
| 5,300,110 | 4/1994 | Latterell et al. ............... 607/130 |
| 5,324,328 | 6/1994 | Li et al. ............... 607/129 |

Primary Examiner—George Manuel
Assistant Examiner—Scott M. Getzow
Attorney, Agent, or Firm—Harold C. Schloss

[57] ABSTRACT

An intelligent patch electrode having a plurality of sensor electrodes for use with an implantable defibrillator. The sensor electrodes are disposed in an array and connected to a microcircuit to sense a depolarization wave as it propagates through the ventricular tissue. The timing, direction of propagation, and point of initiation of successive depolarization waves can also be monitored.

36 Claims, 3 Drawing Sheets

SENSE ARRAY INTELLIGENT PATCH LEAD FOR AN IMPLANTABLE DEFIBRILLATOR AND METHOD

BACKGROUND OF THE INVENTION

The present invention is directed to the design of an implantable defibrillator patch electrode for use with a cardiac pacing and defibrillating device. More particularly, the present invention is directed to the design of an intelligent patch electrode having a number of sensor electrodes. The patch electrode is secured to the exterior surface of the heart to sense electrical activity and deliver an electrical charge to the heart to cause defibrillation.

In order to appreciate the present invention, a fundamental understanding of the physiology of the conduction system in a cardiac cycle is beneficial. Initiation of the cardiac cycle normally begins with depolarization of the sinoatrial (SA) node. A resulting depolarization wave passes through the left and right atria, stimulating their contraction and producing the P-wave of a surface ECG. This depolarization wave proceeds to the junction of the atria and ventricles. A layer of connective tissue separates the atria from the ventricles and serves as insulation, preventing the disorganized passage of current between atria and ventricles. The atrioventricular (AV) node is the normal electrical conduit between atria and ventricles.

Limiting the current passing through the AV node into the ventricle has two important effects. First, excitation of the ventricle begins at a single point, resulting in an organized contraction pattern. Second, conduction through the AV node is slow, which allows time for the transfer of blood from the atria to the ventricles prior to excitation of the ventricles.

Subsequent depolarization of the ventricles also normally follows an organized sequence. Below the AV node, current passes through the short bundle of HIS, then through the left and right fascicles, and through the Purkinje fibers, leading to depolarization of the large ventricular muscle. The time of conduction through the AV node appears on a surface ECG as the longest part of the isoelectric segment between the P-wave and the QRS complex, with a short conduction time through the HIS-Purkinje system. The delay in conduction of the AV node appears on a surface ECG as the isoelectric segment between the P-wave and QRS complex. The orderly progression of depolarization from AV node through the bundle branches and into the ventricles produces nearly simultaneous contraction of the two ventricles.

In comparison, synchronous contraction results when excitation of the ventricles is abnormal, and the conduction of the depolarization wave is not proceeding according to the above description. A wide variety of illnesses may affect the conduction system, including ischemic, inflammatory and degenerative processes. Idiopathic degeneration of the conduction tissue with fibrosis is a common cause of heart block and sick sinus syndrome.

Additionally, tachycardia is the name given to the condition in which the atria, ventricles or both chambers of the heart beat very rapidly, and not within the normal physiological range, typically exceeding 160 occurrences per minutes. Atrial tachycardia is the medical term assigned to the condition in which rapid and regular succession of P-waves of the PQRST waveform complex occur. The rate of occurrence of the P-waves during atrial tachycardia is in excess of the physiological range normally encountered in the particular patient.

Paroxysmal supra-ventricular tachycardia is the medical term assigned to the condition in which there is a sudden attack of rapid heart condition in the atria or in the atrial-ventricular node. The main characteristics are the same as those in atrial tachycardia.

Normally, atrial tachycardia and paroxysmal supra-ventricular tachycardia are not life-threatening conditions, unless they progress into ventricular tachycardia or fibrillation. Ventricular tachycardia is the medical term assigned to the condition in which rapid and regular succession of R-waves of the PQRST waveform complex occur. Again, the rate of occurrence is in excess of the physiological range of the particular patient and can, if untreated, progress into ventricular fibrillation. In ventricular fibrillation, the ventricles are unable to profuse blood in a coordinated fashion and the heart volumetric output drops to a level dangerous to the patient.

In comparison to the normal cardiac cycle which initiates depolarization at the sinoatrial node, ventricular tachycardia or fibrillation results when a depolarization wave propagation is initiated at one or more additional locations or nodes. Thus, while the sinoatrial node may (or may not) be continuing cyclic depolarization, a second or third node located (for example) in the atrium or a ventricle, will initiate depolarization wave propagations at irregular intervals. It should be understood that once a depolarization wave is initiated, it will propagate in a predictable pattern and at a determinable rate through the cardiac muscle.

Typically, life-threatening ventricular tachycardia or ventricular fibrillation requires immediate treatment by drug therapy or by electrical stimulation, such as cardioversion or defibrillation. Implantable defibrillators were developed to monitor the pacing of the heart, and provide a defibrillation charge via a patch electrode attached to, or implanted in, the heart. Implantable defibrillators require sensing capabilities in order to detect the onset of a ventricular tachycardia or ventricular fibrillation. Thus, a defibrillation system usually includes a transvenously implanted sensing lead which includes sensors positioned within the atrium or ventricle to provide continuous sensory data to the implanted defibrillator. Implantable defibrillators allow the recipient a considerable degree of freedom to pursue normal activities, with the defibrillator monitoring cardiac pacing and providing a defibrillation charge promptly upon confirmed detection of ventricular tachycardia.

Accordingly, for certain patients, it is beneficial to affix to the exterior surface of the cardiac muscle a patch electrode which, when electrically connected to an electrical power source, can deliver a large electrical charge directly to the cardiac muscle to cause defibrillation. The electrical energy necessary for defibrillation when delivered by an implanted patch electrode is in the range of, for example, between 1 and 100 joules, but is preferably in the range of between 5 and 40 joules. It is important to recognize that when this amount of power is being coupled directly to the cardiac muscle, there is a potential for severe damage to the tissue. If such damage occurs, the electrical efficiency of defibrillation from the patch electrode in a subsequent application may be severely impaired.

The design of the patch electrode must allow intimate electrical contact over a substantial surface of the cardiac muscle and provide effective delivery of the defibrillation charge. A further consideration of the design of the patch electrode requires, given its location on the surface of the continuously flexing cardiac muscle, that the patch electrode itself be extremely flexible and resistant to fatigue.

With the foregoing in mind, a patch electrode has traditionally been designed simply as a metallic mesh with a polymer insulation backing and an insulating frame. The patch shapes which have been used include both oval shapes and rectangular shapes. Generally, an oval shape allows more intimate contact with the surface of the heart muscle. The insulating backing is normally bonded to the metallic mesh and operates to direct the defibrillation charge into the cardiac muscle.

BRIEF DESCRIPTION OF THE PREFERRED EMBODIMENT

The present invention defines an intelligent patch electrode having discreet sensor electrodes for use with an implantable defibrillator. The sensor electrodes are disposed in an array which allows for the sensing of a depolarization wave as it propagates through the ventricular tissue. The timing, direction of propagation, and point of initiation of successive depolarization waves can be monitored. The monitored data is either compiled or multiplexed in a microcircuit affixed to the intelligent patch electrode and then forwarded to the defibrillator. The use of a plurality of sensor electrodes in the array pattern allows for a degree of precision in monitoring cardiac electrical activity which has heretofore been unavailable.

DETAILED DESCRIPTION OF THE PREFERRED EMBODIMENT

Figure 1:
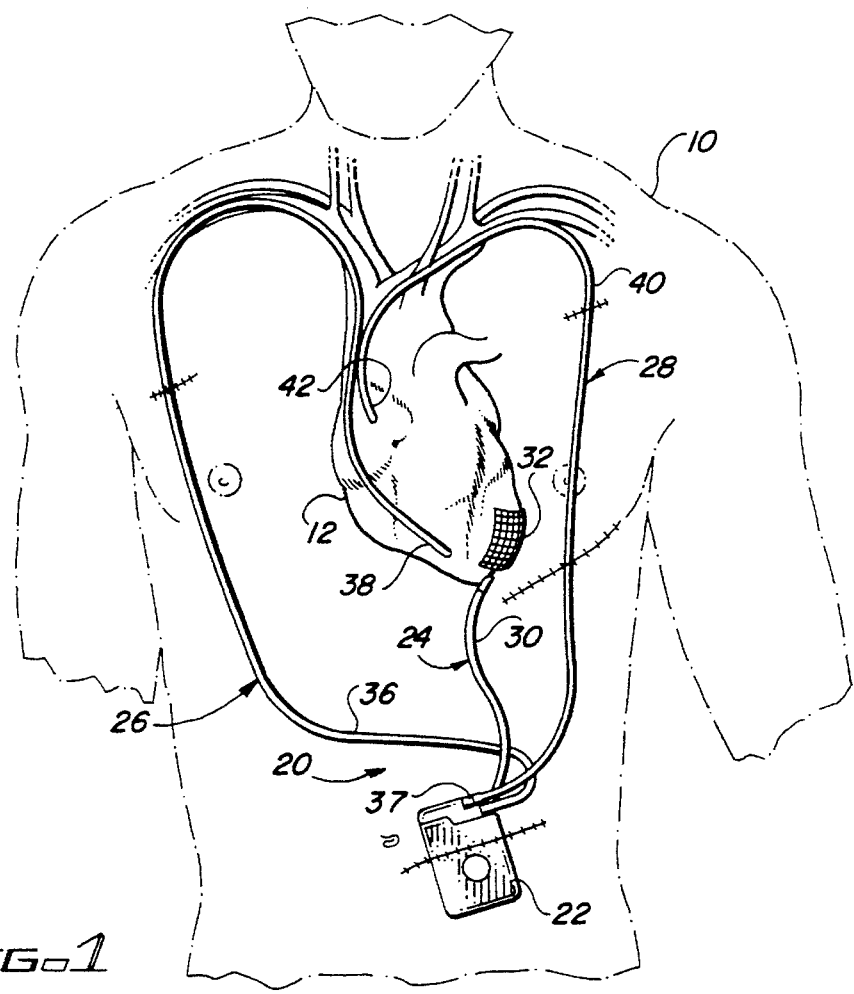
FIG. 1 depicts an implanted defibrillation system having at least one sensing electrode transvenously implanted and a patch electrode affixed to the heart interconnected to a pulse generator.

FIG. 1 depicts a torso 10 illustrating the heart and an implanted cardiac treatment system 20. The cardiac treatment system 20 includes a pulse generator or defibrillator 22 connected with a patch lead 24, a pacing and sensor lead 26, and a vena cava lead 28 to the heart 12. The cardiac treatment system 20 illustrated in FIG. 1 has components typical of those used currently in cardiac treatment systems. Thus, the patch lead 24 includes a lead body 30 connected at its proximal end to the defibrillator 22 via a connector 37 and at a distal end to a defibrillating patch electrode 32 which is affixed to the outer surface of the heart 12. The sensor lead 26 includes a lead body 36 extending from the defibrillator 22. The sensor lead 26 is transvenously implanted into the right subclavian artery, terminating at a bipolar endocardial electrode 38 positioned within the ventricle of the heart 12. The vena cava lead 28 has a lead body 40 extending from the defibrillator 22. The vena cava lead 28 is transvenously implanted into the left subclavian artery, terminating at a superior vena cava defibrillating electrode 42, located in the vena cava or alternatively within the atrium of the heart 12.

Generally, the sensor lead 26 provides bipolar sensing of the ventricle producing electrical signal data indicative of the electrical activity and the depolarization of the heart 12, which is forwarded to the defibrillator 22. The defibrillator 22 includes programmed logic to utilize the sensed cardiac electrical activity data from the sensor lead 26 to monitor the cardiac electrical activity. When ventricular fibrillation occurs, the sensor electrode 38 on the sensor lead 26 sends a signal to the defibrillator 22 which decodes the ventricular fibrillation timing sequence. If necessary, the defibrillator 22 generates a charge which is delivered to the heart via patch electrode 32, or alternatively the superior vena cava defibrillating electrode 42. A unipolar system uses the housing of the defibrillator 22 as the anode. Alternatively, one or the other of the defibrillating patch electrode 32 or superior vena cava defibrillating electrode 42 is used as the anode with the other being used as a cathode in a bipolar defibrillation charge delivery system.

Figure 2:
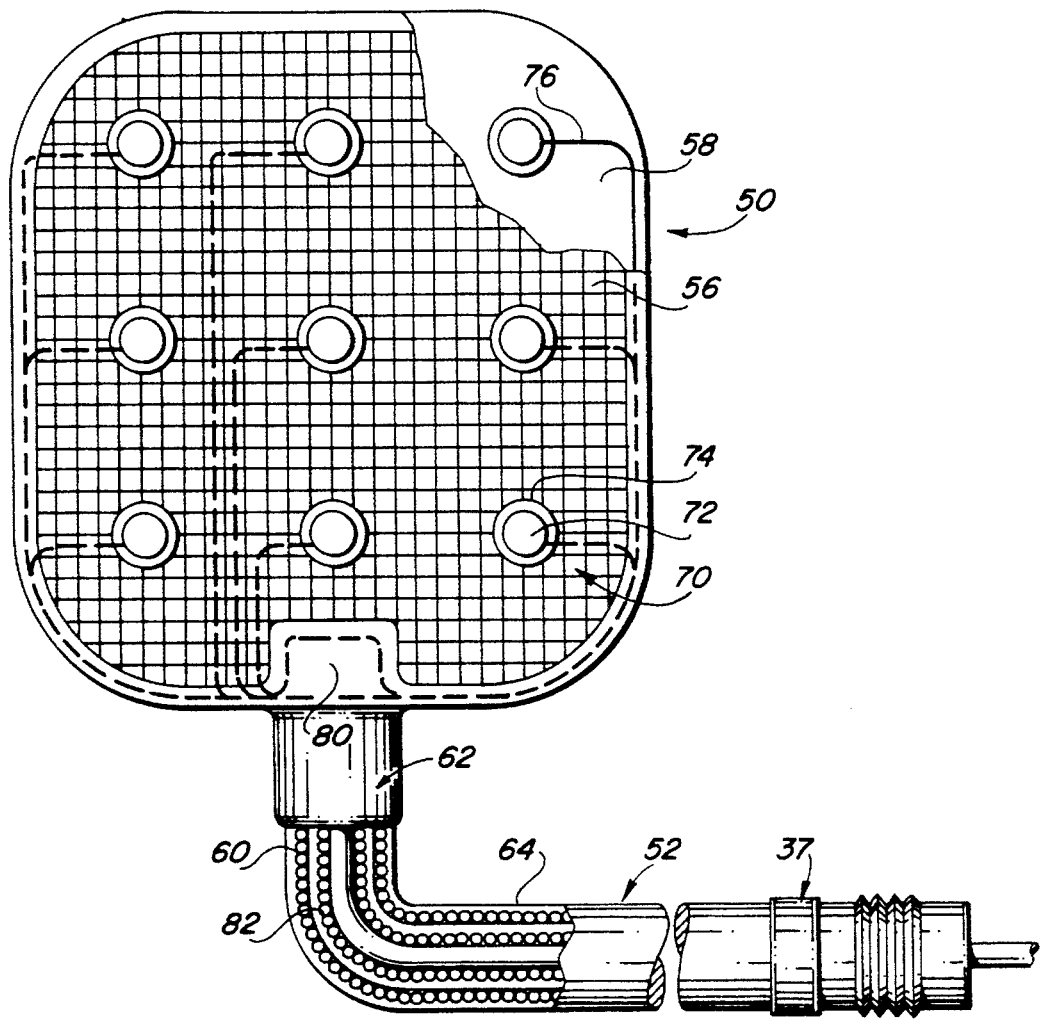
FIG. 2 depicts the intelligent patch electrode of the present invention.

FIG. 2 is a perspective view of the intelligent patch electrode 50 of the present invention. The intelligent patch electrode 50 of the present invention is intended to replace the defibrillating patch electrode 32 shown in FIG. 1, and potentially eliminate the need for any other sensing electrodes. The intelligent patch electrode 50 illustrated in FIG. 2 is connected via a lead body 52 to a pulse generator or the defibrillator 22 such as illustrated in FIG. 1.

The intelligent patch electrode 50 includes a wire mesh 56 affixed to a backing material 58. The backing material 58 is preferably an insulation material such as silicon or rubber. The wire mesh 56 is intended to be flexible and capable of delivering a substantial defibrillation charge. The wire mesh 56 is affixed to a conductor 60 extending through the lead body 52 at a connector assembly 62. The lead body 52 includes the conductor 60 encased within an insulation material 64, and terminates at the connector 37.

The intelligent patch electrode 50 includes a plurality of sensors 70, illustrated as sense electrodes 72 surrounded and insulated from the wire mesh 56 by an insulation ring 74. Each of the sense electrodes 72 is connected to an insulated electrical conductor 76 which extends along the back and edge of the patch electrode 50 to the connector assembly 62. Preferably, each of the electrical conductors 76 is interconnected to an integrated circuit or microchip 80 mounted in the connector assembly 62.

The microchip 80 is preferably a microprocessor or multiplexing chip having a plurality of input points capable of receiving the electrical conductors 76 coming from each of the sense electrodes 72. The microchip 80 also has an output interconnected to a conductor 82 extending through the lead body 52. The conductor 82 may be either wrapped in a side by side helical configuration with conductor 60 in the lead body 52, or may be a helical wound conductor inserted in the center of the helical conductor 60, as illustrated in FIG. 2. It should be noted that the conductor 82 may be a multi-line conductor to provide two or more inputs/outputs to the microchip 80. Thus, the conductor 82 may have a power line for the microchip 80 as well as one or more instruction/data retrieval lines.

Figure 3:
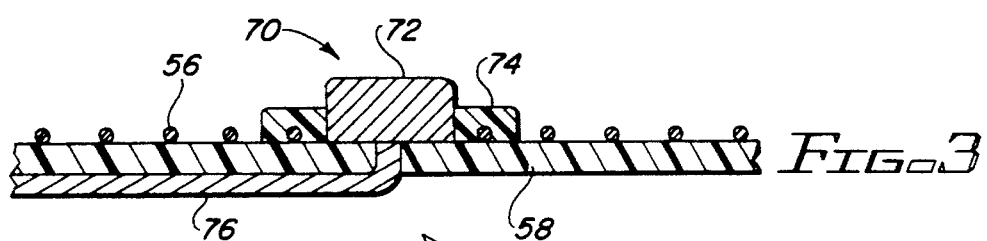
FIG. 3 depicts an enlarged cross-sectional view of a sensor electrode on the patch electrode according to the present invention.

FIG. 3 depicts a cross-sectional view of one of the sensors 70. The sense electrode 72 is shown elevated from the cross-sectionally illustrated wires making up the wire mesh 56. In addition, the insulation ring 74 surrounding the sense electrode 72 is intended to isolate the sense electrode 72 from the individual wires within the wire mesh 56. During construction, it may be necessary to expand the weave of the wire mesh 56 in the area where the sense electrode 72 is to be placed. Also shown in FIG. 3 is the backing insulation 58, as well as the electrical conductor 76 extending from the sense electrode 72 and traversing along the back of the backing insulation 58.

Figure 4:
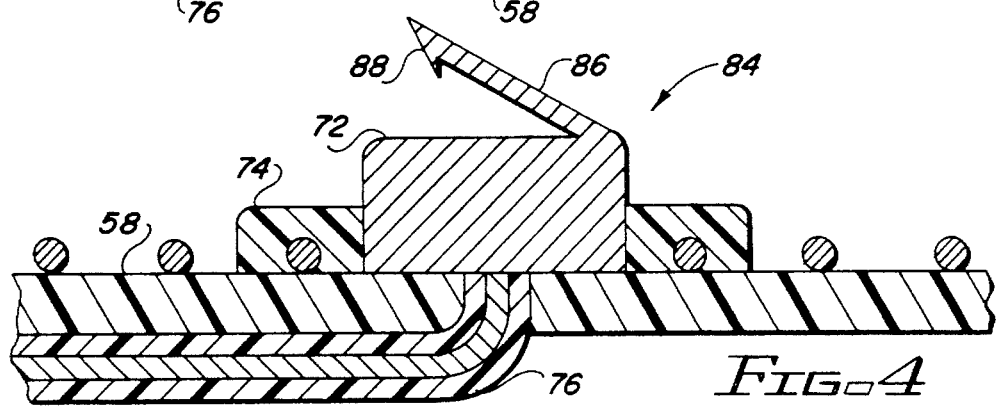
FIG. 4 depicts an enlarged cross-sectional view of an alternative embodiment of the intelligent patch electrode of FIG. 3.

In a first alternative embodiment, an active fixation sense electrode 84 is depicted in the cross-sectional view of FIG. 4. Active fixation sense electrode 84 is illustrated as having a projecting spike 86. The projecting spike 86 may include a barb 88. The spike 86 allows the active fixation sense electrode 84 to positively engage the cardiac tissue when embedded, to provide improved sensing for detecting the electrical activity. The sense electrodes 72, 84 of FIGS. 3 and 4, respectively, are formed from a biocompatible conductive material such as titanium, carbon, titanium nitrate or gold, or a similar material having the requisite biocompatibility and electrical characteristics.

The present invention contemplates forming the patch lead 24 by the steps of providing the wire mesh 56, providing the lead body 30 having electrical conductors 60, 82, and electrically interconnecting the wire mesh 56 to the electrical conductor 60 in the lead body 30. The weave of the wire mesh 56 is expanded in a plurality of locations and the plurality of sense electrodes 72 are inserted through the expanded portions of the wire mesh 56. The sense electrodes 72 are affixed to the plurality of electrical conductors 76, and then bonded to the wire mesh 56 with the insulating ring 74 such that the plurality of sense electrodes 72 are electrically insulated from the wire mesh 56. An insulation backing material 58 is bonded to one surface of the wire mesh 56. The signal processor or microchip 80 is attached to the plurality of electrical conductors 76 to receive electrical signals from the plurality of sense electrodes 72, and the microchip 80 is mounted on the patch lead 24 and interconnected to the electrical conductor 82 in the lead body 30.

The intelligent patch electrode 50 is affixed to the epicardial surface of the heart in a manner such that the sense electrodes 72 are spaced apart and in intimate contact with the cardiac tissue. It should be noted, however, that the intelligent patch electrode 50 can also be placed at a subcutaneous or subcostal site remote from the heart, although this is not preferred.

In either instance, the incorporation of the sense electrodes 72 on the intelligent patch electrode 50 allows for a substantial increase in the capabilities of the defibrillator 22. The multiple sense electrodes 72 can be used to first determine the normal cardiac depolarization activity and to subsequently detect abnormal cardiac depolarization. Specifically, a depolarization wave will traverse across the sense electrodes 72 in a determinable manner. Once a normal depolarization wave propagation is sensed and the normal parameters (e.g. origination point, direction and speed of propagation) are identified and established for a particular patient, the defibrillator 22 can be programmed to look for abnormalities in the sequence in which the sense electrodes 72 detect a depolarization wave front. For example, a normal depolarization wave which initiates at the top right corner of the patch electrode as viewed in FIG. 2 will sweep down from top left to bottom right and cross the sense electrodes 72 in a determinable manner. Once the sequence of electrode excitation is determined, the sense electrodes 72 can monitor subsequent normal cardiac activity, and sense abnormal activity which causes a change in the sequence of excitation of the sense electrodes 72.

Furthermore, the rate at which a normal depolarization wave propagates as well as the normal repetition rate can be monitored. During an abnormal rhythm, a depolarization wave may be initiated at, and propagate from, a different location or node. The intelligent patch electrode 50 can sense a depolarization wave which first appears at the sense electrode 72 positioned at the bottom left corner of the patch electrode as illustrated in FIG. 2, indicating an abnormal wave. In this case, the defibrillator 22 is alerted to the abnormal occurrence and can start a logic sequence to determine whether or not a pacing charge should be delivered to the heart, or whether a defibrillation charge must be delivered.

The sequence for controlling the data stream from the sense electrodes 72 to the defibrillator 22 is preferably programmed into the microchip 80, or the microchip 80 may serve as a multiplexor to forward the data to the defibrillator 22 in a sequential data stream. In either case, the logic for decoding the data from the electrodes 72 is depicted in the flow diagrams of FIGS. 5 and 6. It is to be noted that the flow diagrams are exemplary in nature only, and are not intended to define all of the potential options for using the data from the plurality of sense electrodes 72.

Figure 5:
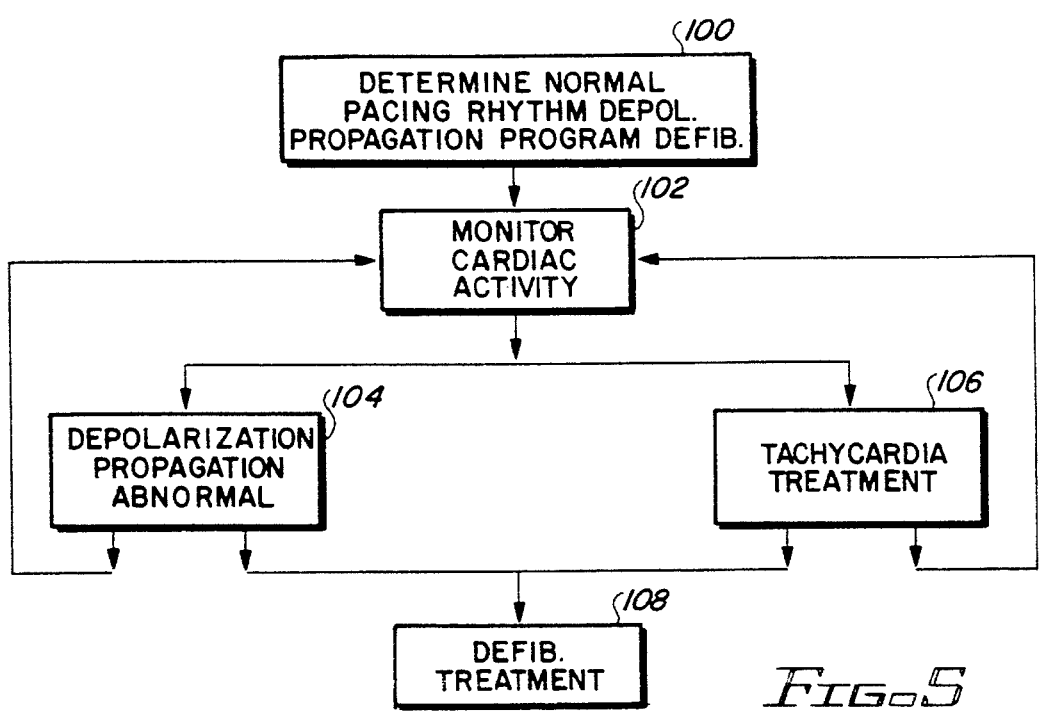
FIG. 5 is a basic operational diagram of a cardiac defibrillation system of the present invention utilizing the intelligent patch electrode.
Figure 6:
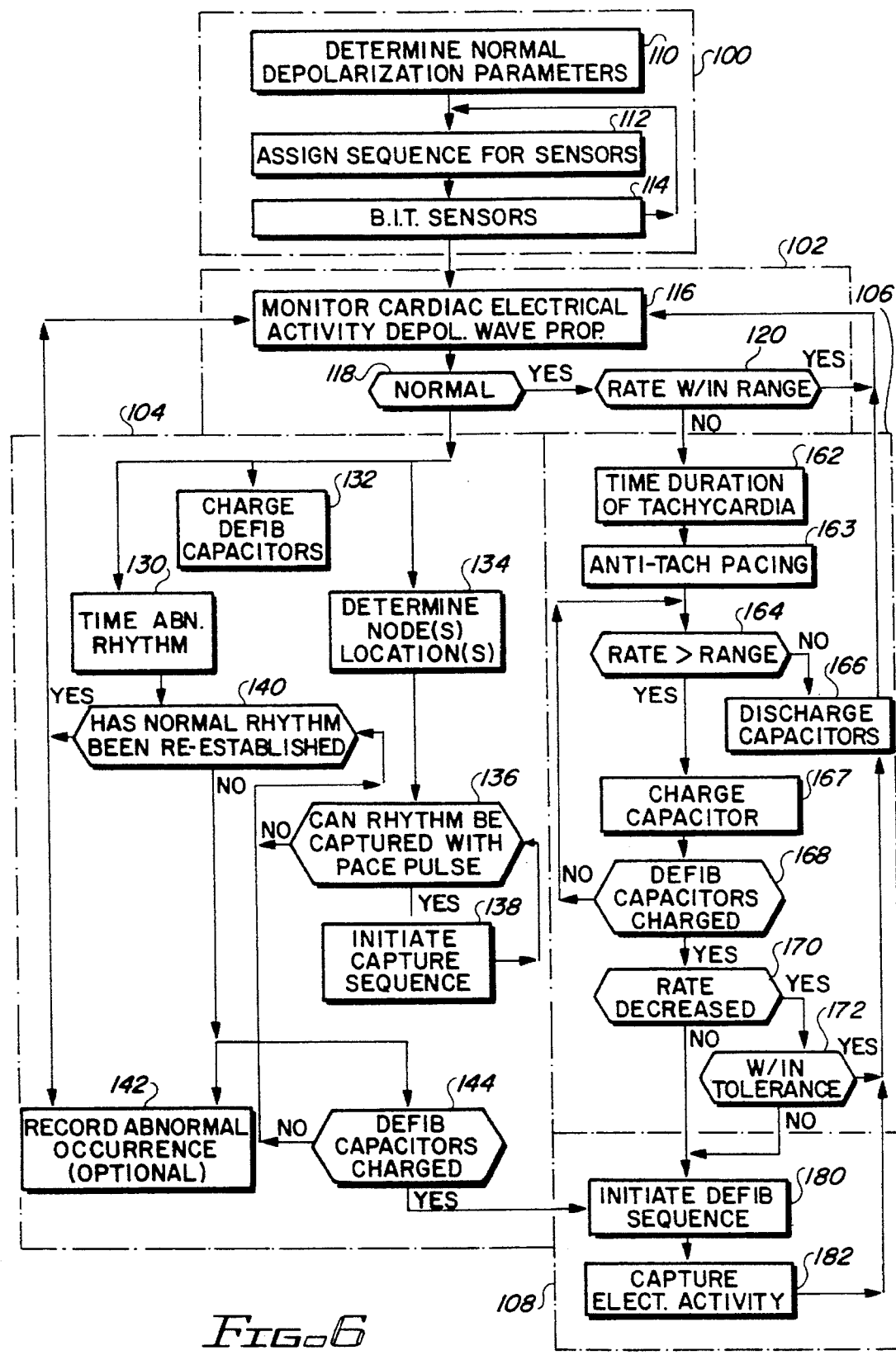
FIG. 6 is a detailed operational diagram of the logic for utilization of the sensor electrode information provided by the intelligent patch electrode.

An example of the logic for controlling and using the data from the plurality of sense electrodes 72 is illustrated in the basic flow diagram of FIG. 5 and the detailed flow diagram of FIG. 6. In the basic flow diagram of FIG. 5, there are five basic steps. The first step is represented by block 100. Following affixation of the intelligent patch electrode 50 onto the heart 12, the cardiac electrical activity is monitored in block 100 to determine the normal pacing rhythm, the depolarization wave propagation pattern, and normal pacing rates for the patient, and the defibrillator 22 is programmed.

The terms "normal" and "established normal cardiac parameters or signals" should be understood herein to refer to the cardiac signals obtained from the patient following implant of the implantable defibrillator patch and the defibrillator 22. The cardiac signals are taken in the absence of a tachycardia or fibrillation, and therefore, are considered to represent the normal patterns of the cardiac electrical activity of the patient. These signals establish the "normal" or standard reference signals or patterns for the depolarization wave propagations against which future sensed depolarization wave propagations are compared. Detecting a departure from the normal cardiac signal patterns tends to indicate a tachycardia condition or fibrillation condition.

It should be understood that the normal cardiac signals are patient-dependent. Accordingly, the attending physician may establish a predetermined range of "normal" values for the cardiac signals, such that existence of cardiac signals within this range is considered acceptable. However, the existence of cardiac signals outside the predetermined range of "normal" signals indicates an abnormal condition, and perhaps a tachycardia or fibrillation, in the absence of extenuating physiological circumstances such as elevation in body temperature or serious bodily injury.

Furthermore, the attending physician may also establish a time period for which a heart rate outside the predetermined range of normal signals may be tolerated prior to the initiation of antitachycardia or defibrillation therapy. The time period or time delay before initiation of therapy allows the patient's cardiac system the opportunity to correct random anomalies without intervention.

The normal cardia parameters and patient specific information are used to program the defibrillator 22 (FIG. 1) and potentially the microchip 80. In the next step, shown by block 102, the system 20 monitors the cardiac activity. This represents, for example, the normal operational status on a routine day-to-day basis for the system 20. The system 20 determines whether the electrical activity of the heart is normal by continuously comparing the repetitive depolarization wave propagations with the standards set in block 100. The system 20 also monitors whether or not the rate of cardiac electrical activity is within an acceptable range.

If in block 102 a determination is made that the depolarization wave propagation has become abnormal, the process proceeds to the steps shown in block 104. Block 104 represents a treatment program for an abnormal depolarization sequence. Following completion of a successful treatment program or abatement of the abnormality, the system 20 returns to the monitoring function shown by block 102.

In the event that in block 102 a determination is made that the rate of cardiac electrical activity is excessive, and therefore that the heart is in a tachycardia sequence, the system 20 progresses to block 106. In block 106, the system 20 monitors and treats a tachycardia sequence. By determining the rate and duration of the tachycardia sequence and making a decision on the appropriate treatment, the system 20 can determine whether a defibrillation shock treatment is necessary. In the event that either a determination is made in block 104 or block 106 that a defibrillation treatment is required, the system 20 proceeds to block 108. In block 108, a defibrillation sequence or regimen is initiated and carried out in an attempt to capture and return the cardiac electrical activity to a normal sequence. Following a successful defibrillation treatment in block 108, the system 20 again returns to the monitoring function of block 102.

This basic sequence is detailed in the block diagram of FIG. 6. In FIG. 6, the blocks 100, 102, 104, 106 and 108 are shown in dashed lines, and the numbered sub-blocks illustrate the subroutines which occur in each of the basic blocks.

Accordingly, in FIG. 6 block 100 is shown as including blocks 110, 112 and 114. Block 110 illustrates the step of determining the normal depolarization parameters following implantation of the system 20. The step contemplates monitoring the normal activity of the heart to establish the basic patterns, and an assignment of the appropriate ranges for normal and abnormal cardiac activity. In block 112, following the initial determination of the depolarization parameters in block 110, the system 20 assigns a sequence for the plurality of sense electrodes 72. The assigned sequence represents the measured "normal" sequence resulting from a normal depolarization wave propagating across the plurality of sense electrodes 72. The sequence will be assigned in order to establish a baseline to subsequently determine whether an abnormal occurrence of a depolarization wave front is occurring. In block 100, the system may also include a built-in test (BIT) routine for the sensors 70, as shown by block 114. The BIT routine is used to make sure that each of the sense electrodes 72 is operative so that the failure of an individual sense electrode 72 will not cause the false generation of an abnormal sequence. If a particular sense electrode 72 is determined to be inoperative, the system 20 will return to block 112 and reassign a new "normal" sequence for the remaining sense electrodes 72.

Proceeding from block 100 to block 102, block 102 is shown as including block 116 wherein the routine monitoring of the cardiac electrical activity is carried out. The primary function in block 116 is to determine whether or not the depolarization wave propagation is within normal parameters. Thus, the sense electrodes 72 are monitored to continuously determine the data stream coming from the sense electrodes 72, and decode their output. In block 118, a determination is made as to whether or not the data output of the sense electrodes 72 is in the proper sequence. When the sequence is normal, the system progresses to block 120 wherein a determination is made as to whether the rate of cardiac electrical activity is within an acceptable range. If the rate of cardiac electrical activity is within an acceptable range, the system returns to the beginning of the monitoring function in block 116.

Returning again to the determination made in block 118 as to whether or not the depolarization wave propagation sequence is progressing according to the established and programmed normal sequence, if the determination is made that the depolarization wave propagation is abnormal, the system proceeds to block 104. Specifically, in block 104, following the determination of an abnormal wave propagation sequence, the system proceeds with the steps of timing the abnormal rhythm in block 130, charging the defibrillation capacitors in block 132, and determining the location(s) of the node or nodes from which the abnormal depolarization propagations are being initiated in block 134.

It is to be noted that each of these steps, block 130, block 132, and block 134 are illustrated as being initiated sequentially although a simultaneous initiation routine may also be utilized. However, the timing limitations for an overall defibrillation sequence are an important factor in determining how the system operates. Thus, it should be recognized that the time required to charge the defibrillation capacitors (not shown) in the defibrillator 22 is generally in the range of between 3 to 10 seconds. In addition, the time required to accurately determine whether a cardiac activity is abnormal, and in addition whether the abnormal activity has occurred for a substantial enough period of time to eliminate the possibility of spurious signals, is generally in the range of between 1 and 3 seconds. Thus, it is desirable to initiate the charging of the defibrillation capacitors at the earliest possible opportunity in order to have the capacitors fully charged if defibrillation is required following an unqualified determination that an abnormal activity is occurring, in order to expedite the defibrillation treatment.

As discussed above, in block 134 a determination of the location(s) of the node or nodes which are initiating the abnormal depolarization wave(s) occurs. From block 134, the system will proceed to block 136 wherein a determination is made as to whether the system can reestablish a proper pacing rhythm by capturing cardiac electrical activity using pacing pulses. These pacing pulses may be delivered using the discreet sense electrodes 72 of the patch electrode 50, or by the use of an implanted pacing and sensor lead 26 (FIG. 1).

In addition, given the spacing of the sense electrodes 72, it is possible to initiated the propagation of a pseudo-normal depolarization wave by selectively and sequentially pulsing the sense electrodes 72. This will be done, for instance, by utilizing the sequence for a normal wave propagation (determined in block 112) and delivering a pacing pulse through one or more of the sense electrodes 72 in accordance with the appropriate sequence for a normal depolarization wave. If a determination is made that the normal cardiac rhythm can be recaptured, the system proceeds to block 138 wherein the capture sequence is initiated by the selective provision of pacing pulses. However, if in block 136 the determination is made that the rhythm cannot be recaptured using pacing pulses, the system moves to block 144 discussed below.

Depending upon the location of the abnormal node, the system can also send small electrical signals to a number of the sense electrodes 72, either simultaneously or in a determinable sequence, to attenuate or cancel the abnormal depolarization wave and prevent ventricular contraction. This treatment or capture sequence, also preformed in block 138, may be successful in certain cases and may be carried out repetitively.

Upon completion of the treatment contemplated in block 138, the system progresses to block 140. In block 140, a determination is made as to whether a normal rhythm has been reestablished. If in block 140 a determination is made that the normal rhythm has been reestablished, the system may record the abnormal occurrence as illustrated in block 142, then the defibrillation capacitors are discharged in block 148 and the system returns to block 102, and specifically the monitoring step of block 116. The recording of an abnormal cardiac occurrence is stored in a memory within the defibrillator 22, and can be recalled by the cardiologist during patient follow up to chart the abnormal sequence(s).

If a determination is made in block 140 that the normal rhythm has not been reestablished, the system progresses to a determination in block 144 as to whether the capacitors in the defibrillator 27 have been fully charged. If the capacitors are not fully charged, the system will return to block 140 to redetermine whether or not the normal rhythm has been reestablished. The system continues in this subroutine until a determination is made within block 144 that the capacitors are fully charged, or within block 140 that the normal rhythm has been reestablished. When it has been determined that the normal rhythm has not been reestablished and that the capacitors are fully charged, the system will progress to a defibrillation treatment illustrated in block 108 discussed below.

Returning to block 102, when a determination is made that the depolarization wave propagation is progressing in a normal sequence in block 118, but that the rate of cardiac activity is not within a proper range in block 120, the system proceeds to the tachycardia treatment shown in block 106. In block 106, the tachycardia treatment begins with the timing of the duration of the tachycardia in block 162. Following the initiation of the timing sequence, the system proceeds to block 163 where antitachycardia pacing is undertaken. Such pacing techniques are well known in the art. (See, for example, U.S. Pat. Nos. 4,541,430 and 4,574,437, which are herein incorporated by reference.) Subsequent to antitachycardia pacing, the system proceeds from block 163 to block 164 where a determination is made as to whether the present tachycardia rate falls outside an acceptable range for an unacceptably long period of time. As discussed above, the acceptable or normal ranges and durations of abnormal rates is preset or programmed into the defibrillator 22 by the physician. By way of example, an unacceptable long period may be in the range of from 5–15 seconds. If in block 164 the determination is made that the pacing rate has returned to within the "normal" ranges, the system will proceed to block 166 wherein the capacitors are discharged and the system then returns to the monitoring function of block 116.

However, in block 164 if the determination is made that the tachycardia rate has continued to occur for a period of time which is greater than the preestablished acceptable range, then the system will progress to block 167 wherein the defibrillation capacitors are charged, and then to block 168 where a determination is made as to whether the defibrillation capacitors have been fully charged. A negative response to the determination in block 168 returns the system to block 164 and the loop continues until the determination is made that the tachycardia activity has occurred for an extended period of time and that the capacitors have been fully charged. Once both of these determinations are made, the system advances from block 168 to block 170 where a final determination is made as to whether the tachycardia rate has decreased. If the tachycardia rate has decreased, the system will make another determination in block 172 as to whether the tachycardia rate is within acceptable tolerances. If the tachycardia rate is within acceptable tolerances, the system returns to block 166 wherein the capacitors are discharged, and the system then returns to block 116 to reinitiate the monitoring sequence. However, in block 170 or block 172 if the determination is made that the rate has not decreased or that the rate has decreased but is not within acceptable tolerances, respectively, then the system will proceed to the defibrillation treatment illustrated in block 108.

In block 108, the defibrillation treatment regimen is illustrated as being a two step process which is initiated either from the depolarization propagation treatment block 104 or from the tachycardia treatment block 106. The defibrillation treatment in block 108 includes a first step 180 wherein the system initiates a defibrillation sequence. Various defibrillation sequences are detailed in the art and will not be described here in great detail. Briefly, however, it is contemplated that the defibrillation treatment in block 108 will progress from a relatively small defibrillation pulse, on the order of 10 to 20 joules, to a larger pulse of 40 to 50 joules over a series of two or three steps in an attempt to capture the cardiac electrical activity utilizing the lowest possible amount of electrical energy. Thus, the defibrillation sequence initiated in block 180 proceeds following application of a defibrillation pulse to a determination of whether there has been a capture of the electrical activity in block 182. Once the cardiac electrical activity has been captured via the defibrillation sequence, the system will reset by routing through block 166, in which the capacitors are discharged, and then returning to the monitoring function of block 102.

The foregoing description of the block diagrams in FIGS. 5 and 6 is intended to detail a number of the features of the present invention. However, it is to be understood that it is not required that all of these features be used or that additional features are foreclosed. Instead, it should be apparent to those skilled in the art that advancements in defibrillators will allow greater usage of the potential for the data stream coming from the plurality of sense electrodes 72 affixed to the intelligent patch electrode 52, as well as additional uses of the sense electrodes 72 as delivery points for electrical stimulus.

It should be evident from the foregoing description that the present invention provides many advantages in the field of implanted defibrillation and patch electrodes. Although the preferred embodiment is specifically illustrated and described herein, it will appreciated that many modifications and variations of the present invention are possible in light of the above teaching to those skilled in the art. It is preferred, therefore, that the present invention be limited not by the specific disclosure herein, but only by the proper literal and equivalent scope of the appended claims.

What is claimed is:

1. A patch lead for use with an implantable defibrillator comprising:

a patch lead body having a first plurality of electrical conductors and a connector at a proximal end for electrically connecting said first plurality of electrical conductors to the implantable defibrillator;

a patch electrode affixed to a distal end of said patch lead body, said patch electrode including a wire mesh mounted on an insulation backing element, said patch electrode being electrically connected to one of said first plurality of electrical conductors;

a plurality of sense electrodes affixed to said patch electrode and electrically insulated from said wire mesh; and microprocessor affixed to said patch electrode and electrically connected to said plurality of sense electrodes, said microprocessor being electrically connected to at least one of said first plurality of electrical conductors of said lead body, said microprocessor processing signals provided by said sense electrodes and producing at least one output signal indicative of cardiac electrical activity.

2. The patch lead of claim 1, wherein said microprocessor is electrically connected to said plurality of sense electrodes by a plurality of second electrical conductors each having one end attached to one of said respective plurality of sense electrodes and opposite ends connected to said microprocessor.

3. The patch lead of claim 1, wherein said microprocessor affixed to said patch electrode is programmed with a sequence representing normal excitation of said plurality of sense electrodes in response to a normal cardiac depolarization wave.

4. The patch lead of claim 1 wherein said plurality of sense electrodes each comprise a conductive element having a surface projecting from the surface of said wire mesh.

5. The patch lead of claim 4, wherein said conductive elements are formed from materials selected from the group consisting of titanium, carbon, titanium nitride and gold.

6. The patch lead of claim 1, wherein said plurality of sense electrodes each comprise a conductive element having a surface, and a projecting spike affixed to said surface of said conductive element, said projecting spike shaped to penetrate the epicardial tissue.

7. The patch lead of claim 6, wherein said conductive elements are formed from material selected from the group consisting of titanium, carbon, titanium nitride and gold.

8. A patch electrode assembly for interconnection with an implantable defibrillator via a lead body having at least first and second electrical conductors, said patch electrode assembly comprising:

a shaped wire mesh, said shaped wire mesh electrically connected to the first electrical conductor of the lead body;

a backing sheet of biocompatible insulating material bonded to one surface of said shaped wire mesh;

a plurality of sense electrodes affixed to said shaped wire mesh;

means for insulating said plurality of sensor electrodes from said shaped wire mesh;

a plurality of electrical conductors each having one end attached to a respective one of said plurality of sense electrodes; and a microprocessor for receiving electrical signals from said plurality of electrodes through said plurality of conductors, said microprocessor being connected to said second electrical conductor of the lead body.

9. The patch electrode assembly of claim 8, wherein said wire mesh is formed from titanium wires and said backing sheet is formed from silicone.

10. The patch electrode assembly of claim 8, wherein said sense electrodes are formed from a biocompatible conductive material.

11. A method of operating an implantable pacing and defibrillator system for monitoring and treating a heart, the defibrillator system including a patch lead having a wire mesh defibrillation electrode and a plurality of sense electrodes mounted on the surface of the heart, the method of operating the system comprising:

using said plurality of sensors for sensing cardiac electrical activity including depolarization occurrences and wave propagation;

determining the rate of depolarization occurrences and direction of propagation of depolarization waves to establish normal cardiac activity parameters and patterns thereof; and monitoring the cardiac electrical activity for depolarization wave propagation patterns which do not coincide with the established normal parameters.

12. The method of operating the implantable pacing and defibrillator system of claim 11, further comprising:

delivering electrical stimulation charges to the heart through said plurality of sensor electrodes of said patch lead in a determinable sequence.

13. The method of operating the implantable pacing and defibrillator system of claim 12, wherein said electrical stimulation charges are delivered to said plurality of sensor electrodes in a sequence to create a pseudo-normal depolarization wave propagation.

14. The method of operating the implantable pacing and defibrillator system of claim 12, wherein said electrical stimulation charges are delivered to said plurality of sensor electrodes to cause cancellation of an abnormal depolarization wave propagation.

15. A method of operating an implantable pacing and defibrillator system for monitoring and treating a heart to which an intelligent patch electrode having a wire mesh electrode and a plurality of sensor electrodes is affixed, comprising the steps of:

sensing the cardiac electrical activity using the plurality of sensor electrodes to determine a pacing rhythm, a depolarization wave propagation pattern, and pacing rates to establish normal cardiac electrical activity patterns;

programming the defibrillator system with acceptable ranges for the established normal cardiac electrical activity patterns;

storing the normal cardiac electrical activity patterns and the acceptable ranges;

comparing subsequent cardiac electrical activity patterns to the stored normal cardiac electrical activity patterns and ranges; and treating the heart using electrical stimulus when the subsequent cardiac electrical activity patterns deviate from the acceptable ranges.

16. The method of claim 15, wherein the step of monitoring cardiac electrical activity further comprises:

comparing depolarization wave propagation patterns sensed by said plurality of sensor electrodes with the established normal standards.

17. The method of claim 15, wherein the step of monitoring cardiac electrical activity further comprises:

monitoring the rate of cardiac electrical activity for the onset of tachycardia.

18. The method of claim 15, wherein the step of treating the heart using electrical stimulus further comprises delivering the electrical stimulus via said intelligent patch lead when subsequent cardiac electrical activity patterns deviate from the stored cardiac electrical activity patterns by more than a predetermined amount.

19. The method of claim 18, wherein the step of treating the heart using electrical stimulus further comprises delivering electrical stimulus via the plurality of sensor electrodes.

20. The method of claim 18, wherein the step of treating the heart using electrical stimulus further comprises delivering defibrillation stimulus via the wire mesh electrode.

21. A patch lead for use with an implantable defibrillator, said patch lead comprising:

a patch lead body having a first plurality of electrical conductors and a connector at a proximal end for electrically connecting said first plurality of electrical conductors to the implantable defibrillator;

a patch electrode affixed to a distal end of said patch lead body, said patch electrode including a wire mesh mounted on an insulation backing element, said patch electrode being electrically connected to one of said first plurality of electrical conductors; and means for providing electrical sensing affixed to said patch electrode and electrically insulated from said wire mesh, said sensing means including means for sensing depolarization wave propagation.

22. The patch lead of claim 21, wherein said sensing means further includes means for determining the rate of depolarization.

23. The patch lead of claim 21, wherein said sensing means further includes means for determining the direction of propagation of depolarization waves.

24. The patch lead of claim 21, wherein said sensing means further includes means for determining when cardiac electrical activity does not coincide with predetermined normal parameters.

25. The patch lead of claim 24, wherein said predetermined normal parameters include a predetermined origination point.

26. The patch lead of claim 24, wherein said predetermined normal parameters include a predetermined direction of cardiac depolarization wave propagation.

27. The patch lead of claim 24, wherein said predetermined normal parameters include a predetermined speed of cardiac depolarization wave propagation.

28. The patch lead of claim 24, wherein said predetermined normal parameters include a predetermined sequence of excitation.

29. The patch lead of claim 21, wherein said sensing means includes a plurality of spaced apart electrodes.

30. The patch lead of claim 29, wherein said spaced apart electrodes include active fixation means.

31. A patch lead for use with an implantable defibrillator, said patch lead comprising:

a patch lead body having a first plurality of electrical conductors and a connector at a proximal end for electrically connecting said first plurality of electrical conductors to the implantable defibrillator;

a patch electrode affixed to a distal end of said patch lead body, said patch electrode including a wire mesh mounted on an insulation backing element, said patch electrode being electrically connected to one of said first plurality of electrical conductors;

means for sensing cardiac electrical activity affixed to said patch electrode and electrically insulated from said wire mesh, wherein said sensing means produces at least one output signal; and signal processing means connected to said sensing means for receiving said at least one output signal from said sensing means and producing a processed output signal, said processed output signal corresponding to cardiac electrical activity.

32. The patch lead of claim 31, wherein:

said means for sensing cardiac electrical activity comprises a plurality of sense electrodes, wherein said at least one output signal comprises a corresponding plurality of output signals, each sense electrode producing a respective one of said plurality of output signals; and said signal processing means comprises switching means electrically interconnected to said plurality of sense electrodes for selectively processing the output signal from each of the plurality of sense electrodes.

33. A patch lead for use with an implantable defibrillator, said patch lead comprising:

a patch lead body having a first plurality of electrical conductors and a connector at a proximal end for electrically connecting said first plurality of electrical conductors to the implantable defibrillator;

a shaped wire mesh, said shaped wire mesh electrically connected to a first one of said first plurality of electrical conductors of said lead body;

a backing sheet of biocompatible insulating material bonded to one surface of said shaped wire mesh;

a plurality of electrodes for sensing cardiac electrical activity affixed to said shaped wire mesh;

means for insulating said plurality of sensor electrodes from said shaped wire mesh;

a second plurality of electrical conductors each having one end attached to a respective one of said plurality of electrodes; and signal processing means for receiving electrical signals from said plurality of electrodes through said second plurality of electrical conductors and producing an output signal indicative of cardiac electrical activity, said signal processing means being connected to a second one of said first plurality electrical conductor of said lead body.

34. A patch lead for use with an implantable defibrillator, said patch lead comprising:

a patch lead body having a first plurality of electrical conductors and a connector at a proximal end for electrically connecting said plurality of electrical conductors to the implantable defibrillator;

a patch electrode affixed to a distal end of said patch lead body, said patch electrode including a wire mesh mounted on an insulation backing element, said patch electrode being electrically connected to one of said plurality of electrical conductors; and a plurality of means for sensing cardiac electrical signals.

35. The patch lead of claim 34, wherein said plurality of sensing means comprises a plurality of sense electrodes affixed to said wire mesh.

36. The patch lead of claim 34, further comprising signal processing means for receiving electrical signals from said plurality of means for sensing cardiac electrical signals and producing an output signal indicative of cardiac electrical activity, said signal processing means being connected to one of said plurality of electrical conductors.

* * * * *